United States Patent [19]

Blades et al.

[11] Patent Number: 4,626,413
[45] Date of Patent: Dec. 2, 1986

[54] INSTRUMENT FOR MEASUREMENT OF THE ORGANIC CARBON CONTENT OF WATER

[75] Inventors: Frederick K. Blades, Boulder; Richard D. Godec, Erie, both of Colo.

[73] Assignee: Anatel Instrument Corporation, Boulder, Colo.

[21] Appl. No.: 569,678

[22] Filed: Jan. 10, 1984

[51] Int. Cl.$^4$ .............................................. G01N 27/07
[52] U.S. Cl. ........................................ 422/78; 422/68
[58] Field of Search .................................. 422/78–80; 436/62, 146, 905; 324/439, 448, 130, 132; 328/114, 132, 165; 307/517, 491; 364/571, 497

[56] References Cited

U.S. PATENT DOCUMENTS

| | | | |
|---|---|---|---|
| 3,738,812 | 6/1973 | Berry et al. | 324/439 |
| 3,958,941 | 5/1976 | Regan | 23/253 |
| 4,140,018 | 2/1979 | Maldcarelli et al. | 73/864.22 |
| 4,227,151 | 10/1980 | Ellis et al. | 324/448 |
| 4,272,679 | 6/1981 | Blades | 250/372 |
| 4,293,522 | 10/1981 | Winkler | 204/1 T |
| 4,304,996 | 12/1981 | Blades | 250/373 |
| 4,357,668 | 11/1982 | Schwartz et al. | 364/497 |
| 4,418,566 | 12/1983 | Beck et al. | 73/23 |

FOREIGN PATENT DOCUMENTS 2029015  3/1980  United Kingdom .................. 436/60

OTHER PUBLICATIONS

Stephen J. Poirier et al., "A New Approach to the Measurement of Organic Carbon" Reprint for American Laboratory, Dec., 1978.
"Photochem Organic Carbon Analyzers", Sybron Corporation Analytical Products.

Primary Examiner—Barry S. Richman
Assistant Examiner—Michael S. Gzybowski
Attorney, Agent, or Firm—Saidman, Sterne, Kessler & Goldstein

[57] ABSTRACT

Apparatus and methods for measurements of total organic carbon content of water, particularly of low relative organic content, is described which features a single sample cell for exposure of a sample to ultraviolet radiation comprising electrodes for measuring the resistivity of the water. The conductivity is monitored as a function of time and the second time derivative of the conductivity signal is monitored to indicate when the oxidation reaction has been completed. Compensation for the contribution to conductivity of the water sample made by the instrument is achieved by subtracting a quantity porportional to the first time derivative of the resistivity at a time when the second time derivative reaches zero, indicating that the oxidation reaction is complete, from the overall conductivity measurement, the remainder being equal to the contribution of conductivity made by the organic content to the water.

19 Claims, 10 Drawing Figures

INSTRUMENT FOR MEASUREMENT OF THE ORGANIC CARBON CONTENT OF WATER

FIELD OF THE INVENTION

This invention relates to instruments for the measurement of the total organic carbon (TOC) content in water. More particularly, the invention relates to instruments for accurately measuring low levels of organic carbon in pure or ultrapure water streams.

BACKGROUND AND OBJECTS OF THE INVENTION

Modern high technology manufacturing processes often use highly purified "ultrapure" water in large quantities. The semiconductor industry in particular uses ultrapure water as a universal solvent in virtually every step of the production of integrated circuits. In recent years, it has been recognized that even trace amounts of organic contamination in the water, though often undetectable by the commonly-used ionic (i.e. resistivity-based) measurement techniques can severely degrade both product quality and yield. Accurate and continuous monitoring of the total organic content is crucial if these problems are to be avoided. Similar problems exist through other industries, such as pharmaceutical and chemical manufacturing.

Several prior art approaches to measurement of the organic content of water have been proposed. Those relevant to the present invention are primarily concerned with oxidation of the carbon in the organic material to carbon dioxide and then measuring the carbon dioxide content. This has been done in the past in several ways. The fact that carbon dioxide is an absorber of infrared light has been utilized. The oxidation has also been performed in several ways, including combustion, and using chemical oxidizers such as perchlorates. These methods are clumsy and the replete with the potential for significant errors, particularly in the low-TOC area addressed by the present invention. More relevant to the present invention is the approach shown in U.S. Pat. No. 3,958,941 to Regan, in which ultraviolet light is used to oxidize the carbon-containing organics to carbon dioxide. The carbon dioxide is then transported to a pure water sample, and the change in conductivity of the pure water due to the presence of the additional ionic species is monitored to determine the amount of organic material thus oxidized. Oxidation of the organics to $CO_2$ and measurement of the change in the water's conductivity are used by the apparatus of the present invention. However, several improvements over the Regan apparatus are shown herein.

The Regan apparatus, which is commercially available, is proposed as a tool for measuring organic content of water over a wide range, from the parts per million (ppm) range through parts per thousand and, indeed, even higher. Applicants have had experience with this apparatus, however, and find that the problems inherent in total organic carbon measurement at extremely low dissolved organic levels, on the order of one part per billion (ppb) to one ppm are such that a different type of apparatus should be used for these extremely low level measurements. Thus, while the Regan approach is workable, it is of primary utility in the areas of relatively high organic concentrations.

The Regan apparatus requires the operator to perform several independent preliminary measurement runs to determine the "instrument contribution" or background level of the instrument. The applicants have found that the values determined in such measurements tend to change with time, thereby requiring frequent "calibration" runs to maintain measurement accuracy.

The Regan apparatus assumes a fixed time for the oxidation process to go to completion. If the organics present in the sample are difficult to oxidize, or if the ultraviolet lamp has aged so as to produce insufficient oxidizing radiation, they may not be completely oxidized in the time allotted, thus leading to misleadingly low measurements. Furthermore, if the level of organics is very low and oxidation proceeds to completion rapidly, the interference caused by instrument contribution may contribute significant errors.

It is therefore a further object of the invention to provide an instrument whereby the oxidation process can be monitored so that its actual completion can be accurately and readily determined.

As mentioned, the Regan apparatus provides a two-loop system, in which the organics in water are first oxidized by exposure to ultraviolet (UV) light, and the resulting carbon dioxide transferred to a measurement chamber, where it is dissolved in pure water, the conductivity is thereafter measured. The conductivity is thus measured in a different chamber than that in which the ultraviolet light is exposed to the water. This has the highly significant defect that transport of the carbon dioxide between the UV exposure chamber to the conductivity measurement chamber is obviously required. The present invention is designed to address measurement of the organic content of water in such low concentrations that any minor impurities which are added to the water by this or any comparable transport system (as well as loss of $CO_2$) can very greatly affect the accuracy of any measurement.

Accordingly, it is an object of the invention to provide an instrument for the measurement of total organic carbon in water which avoids water, $CO_2$ or other material handling or manipulative steps such that the impurities inevitably added in such steps are avoided.

The present invention overcomes the problems associated with the defects of the Regan apparatus due to its transport and manipulative step requirements by providing a single chamber in which the ultraviolet radiation is exposed to the water and in which the conductivity measurements are made. This has several advantages, among which are, of course, reduction of pollutants or contamination due to transport, simplicity and low cost. Furthermore, the fact that the electrodes can be and are in a preferred environment exposed directly to the UV light means that there is no or very little chance of organic fouling of the electrodes, another problem inherent in the Regan apparatus according to the two-chamber approach proposed thereby.

It is accordingly an object of the invention to provide an instrument for measurement of total organic carbon in water in which a static water sample is measured for background conductivity, is then exposed to ultraviolet light, and variation in its conductivity is measured over time, without movement from a single sample chamber, whereby inaccuracies due to manipulative steps are eliminated.

It is a further object of the invention to provide such an organic matter measurement instrument in which the electrodes used for conductivity measurement are directly exposed to the ultraviolet light used to oxidize the organic carbon to carbon dioxide, such that organic fouling of the electrodes is avoided.

It is a further object of the invention, in accordance with good design practice, to avoid use of materials in contact with the water sample which could lead to leaching of additional impurities, such as iron, polyethylene, and other materials found in the prior art designs, and instead to permit only relatively inert materials such as Teflon (trademark of DuPont Corporation) or quartz to come into contact with the water sample.

As mentioned above, according to the invention, it is desired that a static water sample be examined; that is, according to the invention, a water sample is taken from the process of interest. The testing according to the invention is tnus not an in-line process, as that term is typically used, although, in fact, the time taken for a typical measurement, on the order of one to ten minutes, is such that substantially up-to-date information can be provided. The prior art generally teaches away from such static measurements, because it is known that the materials comprising the electrodes used for the conductivity measurements as well as those of the sample chamber tend to be leached out into the water stream and make some contribution to the conductivity of the water. The more delicate the measurement, the more serious these contributions can be. Use of a flowing water stream has been suggested to minimize the effects of such additional ions which alter the conductivity.

It is a further object of the invention to provide a means by which the instrument contribution or "background" conductivity can be determined and subtracted from the total measured value for conductivity, as the oxidation reaction proceeds, permitting use of a static sample measurement.

According to the present invention, accurate compensation is made for the instrument contribution due, e.g., to its materials leaching over time, so that the other advantages of static measurement can be realized, and so that the instrument contribution to conductivity, regardless of its source, is prevented from interfering with accurate measurement.

As mentioned, according to the process of the Regan patent, the conductivity of the water in a measurement chamber is first measured. The water sample of interest is exposed to ultraviolet light in a second exposure chamber for a fixed length of time. The carbon dioxide is then removed and dissolved into the water in the measurement chamber. The conductivity of the water is then measured and compared to its conductivity at the beginning of the exposure period. The difference is taken to be indicative of the change in conductivity due to oxidation of organic carbon. Because the relationship of conductivity of water to carbon dioxide content is known, this can be used to directly derive a measurement of organic carbon content. There are several difficulties inherent in this approach. One is that the background noise or instrument contribution, including the additional conductivity caused by leaching of organic or inorganic materials of the apparatus, is not repeatable over time, a fact brought out by the applicants' experiments. Furthermore, the dependence of resistivity of water on carbon dioxide content is not a linear function, but is exponential, such that at higher organic carbon contents, relatively little conductivity change is experienced with significant variation in organic carbon content. Hence, accurate determination of the background level is essential if an accurate measurement of organic content is to be provided.

Accordingly, it is an object of the invention to provide a method and instrument for measurement of the organic content of water in which accurate background compensation is made, yet in which background compensation is not dependent on repeatability of background measurement, and wherein compensation is made for increased chemical activity of the sample chamber caused by ultraviolet light, and wherein the compensation for background is sufficiently delicate that the precision of result necessary for distinguishing between conductivity caused by various relatively low amounts of organic content is made possible.

One primary difficulty with prior art TOC measuring instruments is that all presently available devices require frequent and tedious calibration, due largely to the high and somewhat varying instrument contribution or background.

Accordingly, it is an object of the invention to provide a TOC measuring instrument, the absolute calibration of which is made solely by correctly calibrating the integral temperature-corrected conductivity sensor.

It is a further object of the invention to provide a TOC measuring instrument which automatically detects and compensates for such spurious background, substantially eliminating the need for frequent calibration.

SUMMARY OF THE INVENTION

The present invention achieves the needs of the art and objects of the invention mentioned above by its provision of an instrument for the measurement of the total organic content of water. The instrument comprises a single sample cell with two electrodes exposed directly to the incident ultraviolet light arriving from an ultraviolet source. The conductivity of the water is measured to establish a background value with no incident UV light, and then the UV lamp is switched on, exposing the sample to oxidizing radiation. The conductivity of the water is measured and recorded over time. In a preferred embodiment, a dedicated computer device is used to monitor changes in the conductivity of the water over time. The computer is used to separate the changes in conductivity due to production of $CO_2$ from changes due to background instrument contributions. The method of differentiation of conductivity caused by background contamination from oxidized organics producing $CO_2$ is based on the relative state of completion of the two processes.

In the case of oxidation the process is brought to completion within a short period of time, i.e., 1-5 minutes. It is therefore a substantially non-linear function, asymptotically approaching its final value in a relatively short period of time.

The background contamination, on the other hand, is to a degree a function of extremely small quantities of contaminants diffusing into the sample during the oxidation period, thus producing a gradual increase in sample conductivity not related to the production of $CO_2$. Since the level of contaminants diffusing during this oxidizing period is likely several orders of magnitude below saturation, the conductivity function due to this contribution is substantially linear and can therefore be mathematically differentiated from the non-linear production of $CO_2$. Other mechanisms may also add to the instrument contribution; it appears that these too do not reach equilibrium in the relatively short period of time during which the oxidation reaction is completed, and are linear during that period. Differentiation between the linear instrument contribution and the non-linear oxidation contribution is accomplished by observing the second time derivative of the conductivity of the water. When the second derivative becomes zero, within a predetermined measurement accuracy limit, this indicates that the oxidation reaction has been completed. The first time derivative of conductivity is also monitored; its value at the time the second derivative reaches zero is the "slope" of the background conductivity curve, due to the instrument contribution, and can be used to derive an indication of the total background noise, which can then be subtracted from the measured total conductivity, such that the remainder is the resistivity proportional only to total organic carbon content. Where the first time derivative of the data becomes zero or negative, the background conductivity can, in general, be disregarded.

BRIEF DESCRIPTION OF THE DRAWINGS

The invention will be better understood if reference is made to the accompanying drawings, in which.

BRIEF DESCRIPTION OF THE PREFERRED EMBODIMENTS

Figure 1:
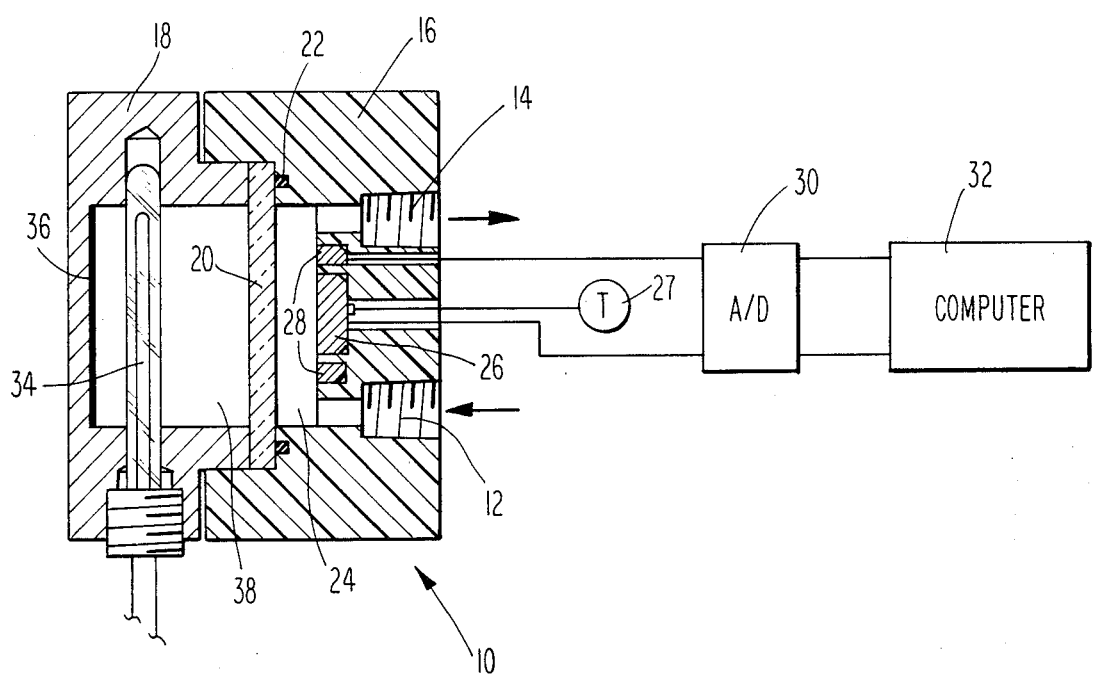
FIG. 1 shows a cross sectional view of the cell of the instrument according to the invention and shows schematically its connection to other parts of the apparatus.

A typical sample cell according to the invention is shown at 10 in FIG. 1. This cell is arranged to be connected at port 12 to a source of influent water, to be tested for the presence of organic carbon. The effluent water exits at port 14. Control valves (not shown) may be provided if necessary. In a high purity system, these may be of Teflon or similarly relatively inert materials. Typically, as noted, the process stream from which the water sample is taken may comprise such things as the water in a semiconductor processing line, pure water used in pharmaceutical manufacturing, organic chemical research, bioengineering, and other high precision laboratory and industrial operations.

The cell 10 comprises two main body portions 16 and 18. Body portion 16 is preferably formed of Teflon, ensuring that a minimal quantity of impurities are leached out into the water stream. A recess in the Teflon body 16 is covered by a quartz window 20, quartz also being an inert material, thus defining the sample chamber 24. In cases of high pressure systems, it may be necessary to take steps to limit the pressure on the window 20. Fastening devices such as screws not shown) connecting the two body portions 16 and 18 compress the quartz window 20 into an O-ring 22, ensuring a fluid-tight chamber 24. Within the fluid-tight chamber 24 are disposed two concentric circular electrodes 26 and 28, respectively, which may in a preferred embodiment, be made of titanium, or another electrode material chosen for resistance to diffusion; palladium, iridium, rhodium and platinum are some possible alternatives. In the preferred embodiment, the electrodes may be chamfered as shown, and are an interference fit within the Teflon body portion 16, ensuring a good seal therebetween. The concentric electrode arrangement has several advantages. Chief among these is that the cell constant of this arrangement is quite high, ensuring relative sensitivity of the instrument to changes in conductance, whereas the capacitance between the two elements 26 and 28 is relatively low. As shown, the electrodes fit flush to the wall of the chamber; this discourages the formation of bubbles, fouling, and the like. A conventional temperature sensor 27 can conveniently be attached to the rear of the central electrode 26; this is used to compensate for variation in sample conductance with temperature. The titanium electrodes are connected to a conventional analog/digital converter device 30 and then to a computer or similar data processing device 32 for monitoring changes in resistance of the water in the chamber 24 over time. An ultraviolet lamp 34 is inserted through an orifice in the body portion 18, and this can be energized to supply ultraviolet light. The lamp 34 may be of the type known in the art as a low-pressure mercury vapor lamp. This class of lamp is chosen because its radiation is at primarily 253.7 nanometers wavelength with some 3% at 185.0 nanometers wavelength. Use of the 185.0 nanometer radiation, which is desired because light of this wavelength is very destructive to organic molecules, requires that the quartz window 20 be of a material which transmits this light well; a glass known as Supersil from Ameresil Co. works well. Similarly, the amount of water in the cell is deliberately kept small. The back of the chamber 38 formed in the body 18 may be mirrored as indicated at 36 to ensure high efficiency use of the ultraviolet light. The chamber 38 within which the lamp is located is desirably filled with dry nitrogen or other non absorbing gas. If it were filled with air or oxygen, for example, the oxygen would absorb some substantial fraction of the ultraviolet light emitted by the lamp 34.

Thus, in use, a sample of water from a process of interest is admitted to the chamber 24 and an initial background conductance reading is taken. The ultraviolet lamp is turned on, and the conductance of the water is monitored as a function of time by the computer 32. When the results of this monitoring indicate that the organic reaction has been completed, detected in a manner discussed in detail below, thus indicating that all the carbon in the organic matter has been converted to carbon dioxide, an output indicative of the total organic carbon content of the influent sample can be generated in accordance with the known relationship of carbon dioxide content in water to its conductance. See, e.g., *A New Approach to the Measurement of Organic Carbon*, Poirier et al. *American Laboratory*, Dec. 1978, in which this relationship is shown. Note that in general, the water samples monitored contain sufficient oxygen that no additional oxidizers are required. If not, the use of oxidizing chemicals such as perchlorate should be avoided, as they are a source of additional impurities, in favor of pure oxygen.

The use of the single sample chamber 24 as shown in FIG. 1 has several advantages. Probably the primary among these is that no movement of water or carbon dioxide between an irradiation chamber and a conductance measurement chamber is required, as in the prior art Regan patent, thus greatly lessening the opportunity for impurities and contaminants to leach out from the instrument and associated support system in contact with the sample which would be required if such an approach were employed. Furthermore, the direct exposure of the electrodes 26 and 28 to the UV light emitted by the lamp 34 serves to keep them free of organic contaminants and the like. The net result is that generally the instrument itself is the only serious source of misleading ionic species in the water, "misleading" in the sense that it contributes spurious conductance not caused by oxidized carbon compounds. Accordingly, means must be found for compensation for these inaccuracies. This is particularly important in the case of low carbon level measurements, on the order of 100 ppb and less, because there the leaching of instrument materials such as the titanium of the electrode is sufficiently rapid that the conductance does not stabilize as a function of time, i.e., the titanium continually leaches at a rate such that the conductance appears to continually rise. Similarly, even if the instrument is made of a relatively inert material such as Teflon, this material can make a spurious contribution. A similar effect, though of different sign, can occur due to absorbtion of the carbon dioxide by the Teflon. Other instrument contributions are doubtless possible. In a manner now to be described, the instrument and system of the invention differentiates between all instrument contributions, which occur at a relatively constant rate during the period of the oxidation of the carbon, and the conductivity contribution of the carbon dioxide, at low-TOC concentrations. In such cases, the conductance value never stabilizes, because the instrument contribution continues. At higher organic concentrations, this is less of a problem, because there the instrument contributes relatively less to the total conductance of the water solution, and the conductance stabilizes to within experimental error to the asymptote of the conductivity curve due to oxidation of organics.

Figure 2:
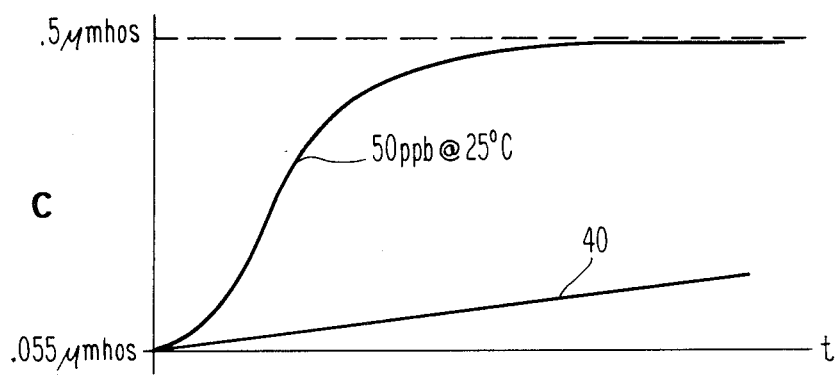
FIGS. 2 through 9 show various curves useful in understanding the operation of the system of the invention.

FIG. 2 shows an idealized plot of the conductivity of water corrected for temperature and instrument background variations, the organic carbon content of which is being oxidized by ultraviolet light, versus time. Here the vertical axis is conductivity C, which can vary from the conductivity of pure water, 0.055 micromhos at 25° C. at the origin to on the order of 0.5 micromhos for 50 ppb organic-carbon contaminated water through perhaps 5 micromhos at water contaminated at 5 ppm, both again at 25° C. It will be observed that the exemplary curve shown approaches an asymptotic limit, which is usual. Typically, this limit will be approached in on the order of one to five minutes after commencement of exposure of the water to ultraviolet light. It will also be observed that the curve is substantially non-linear.

Figure 3:
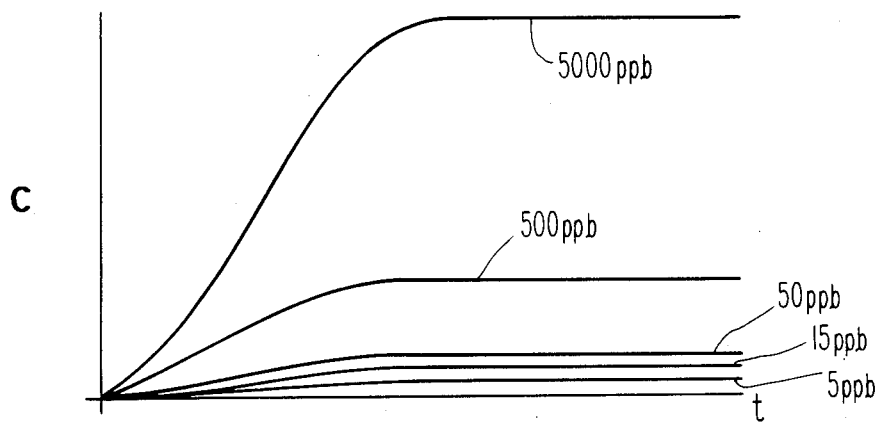

FIG. 3 shows a number of additional curves of the conductivity of water samples containing various amounts of organic carbon, as noted, being oxidized as a result of exposure to ultraviolet radiation as a function of time. It will be observed that the relative differences between the asymptotic portions of the curves for widely varying concentrations of contaminants are not very great, particularly in the high-TOC region. That is, the ultimate conductivity of water samples after oxidation of relatively widely varying amounts of organic material are quite similar. Accordingly, if these samples are to be distinguished from one another by measurement of conductivity, any background noise or other spurious contribution must be rigorously eliminated, and the present invention is designed to achieve this goal.

Figure 4:
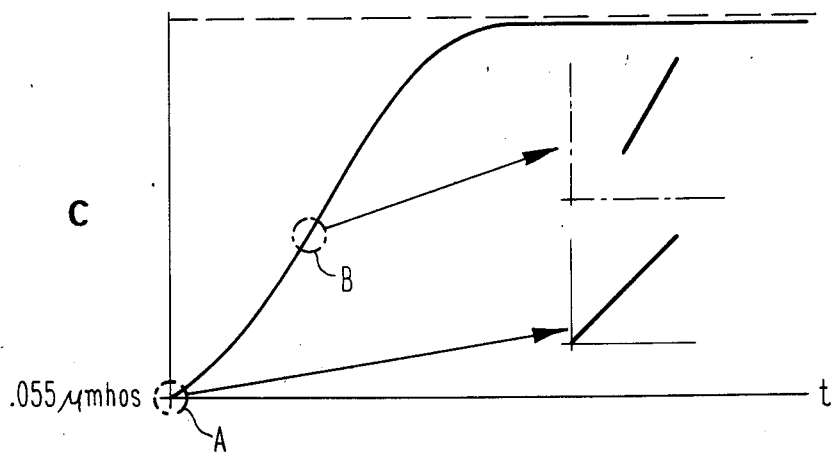

FIG. 4 shows a curve of the temperature corrected conductivity of organic free water sealed in the sample chamber and irradiated with ultraviolet light as a function of time, varying due to leaching of titanium into the water, or other instrument contribution. Here the time scale is on the order of several days. It will be observed that this curve also approaches an asymptotic limit as the water becomes saturated by the instrument contribution but that the portion of the curve of interest, that within a circle A of a few minutes' radius around the origin, as shown enlarged on the right side of FIG. 4, is relatively linear. As indicated at B, other small portions of the total curve are also substantially linear. Again, the origin is at 0.055 micromhos, the conductivity of pure water, and the conductivity can rise to a very high value in the case of saturated water. However, the time required for approaching the saturation point is on the order of days.

If one expands the very leftmost portion of the curve of FIG. 4, indicating variation of conductivity due to the instrument contribution and inserts this at 40 into FIG. 2, showing variation in conductivity due to oxidation of organic material to carbon dioxide, and sums the two curves, thus providing a curve indicative of the typical shape of real data detected in measurements made according to the invention, the horizontal portion of the curve of FIG. 2 will be replaced instead with a linear portion superimposed upon the non-linear portion of the curve of FIG. 2, and this is what is observed.

Figure 5:
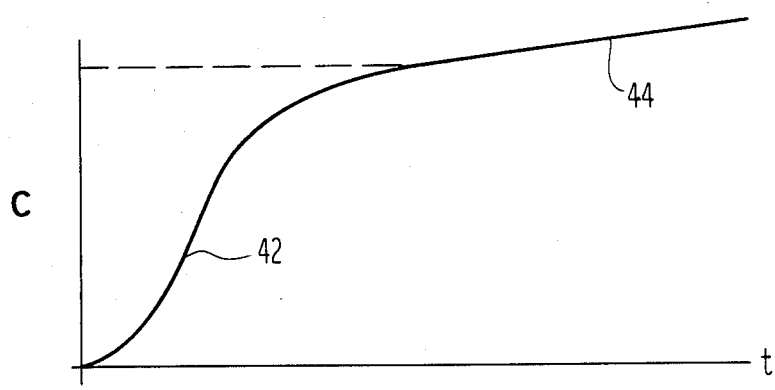

FIG. 5 shows an example of typical test data of this kind. The non-linear portion 42 of the curve is similar to that of FIG. 2, whereas the linear but non-horizontal portion 44 is the result of the addition of the linear portion of curve 40 of FIG. 2 due to instrument background.

Figure 6:
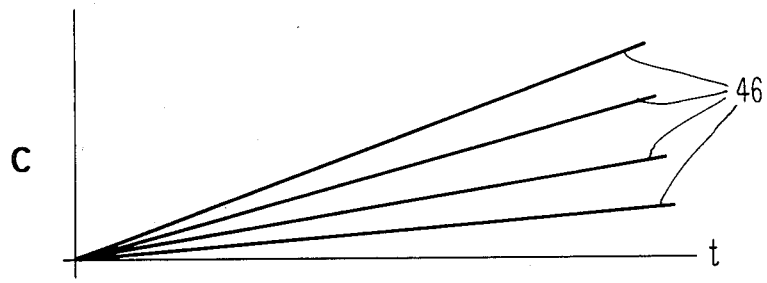

It might be considered, therefore, to be a simple matter to measure the curve of saturation of a typical instrument design, curve 40 of FIG. 2, e.g., at initial manufacture of the instrument, and subtract this from actual test data so as to yield a compensated curve. However, in fact this does not yield accurate results. FIG. 6 shows one reason why. The several curves 46 shown there all correspond to the curve 40 in FIG. 2 and indicate that while the instrument contribution may be relatively linear for the several minutes during which a given TOC measurement is made this rate is not the same for all samples and under all circumstances, so that these measurements are not repeatable, preventing a base line measurement from being established for correcting test data as suggested. Furthermore, it appears likely to the applicants that exposure of the instrument material to ultraviolet light may also increase its contribution in a not entirely predictable fashion, such that this effect would similarly lead to inaccuracies if simple subtraction of a baseline correction were made to actual experimental data. Accordingly, more sophisticated techniques for determining when the organic carbon oxidation reaction is complete and for calculating the correction to be applied are required, and these are provided by the invention as well.

Figure 7:
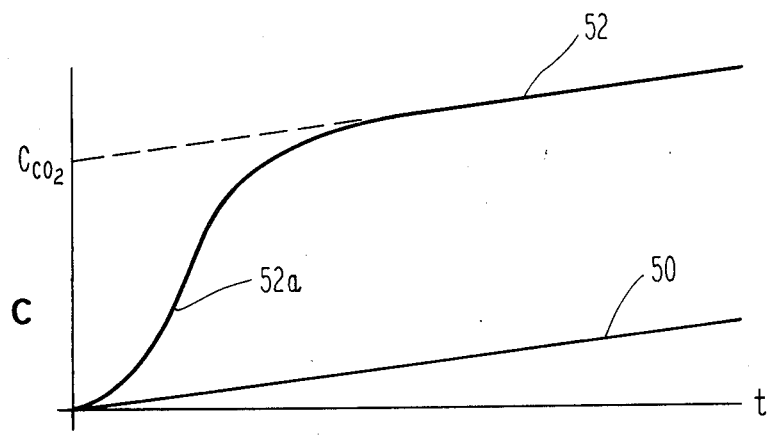

FIG. 7 shows an enlarged view of a curve comparable to that shown in FIG. 5 illustrating the differentiation between the instrument conductivity contribution versus time curve 50, which is substantially linear for the short time (e.g. 1-10 minutes) shown and the curve 52, which plots measured conductivity versus time data. The non-linear portion 52a of curve 52 is that due to oxidation of carbon components to form carbon dioxide. Once this reaction is essentially complete, curve 52 also becomes linear. The subsequent increase in temperature corrected conductivity is due solely to the instrument contribution. Therefore, the linear portion of curve 52 can be extended leftward to the conductivity axis, where the intercept $C_{CO_2}$ provides a measure of the difference in conductivity between the total curve 52 and the portion 50 contributed by the instrument, i.e., a measure of the portion contributed solely by the carbon dioxide resulting from oxidation of organic carbon. This value for conductivity $^{C}CO_2$ can then be directly converted to a value for total organic carbon in the sample, e.g., using the data shown in the article by Poirier et al referred to above.

Figure 8:
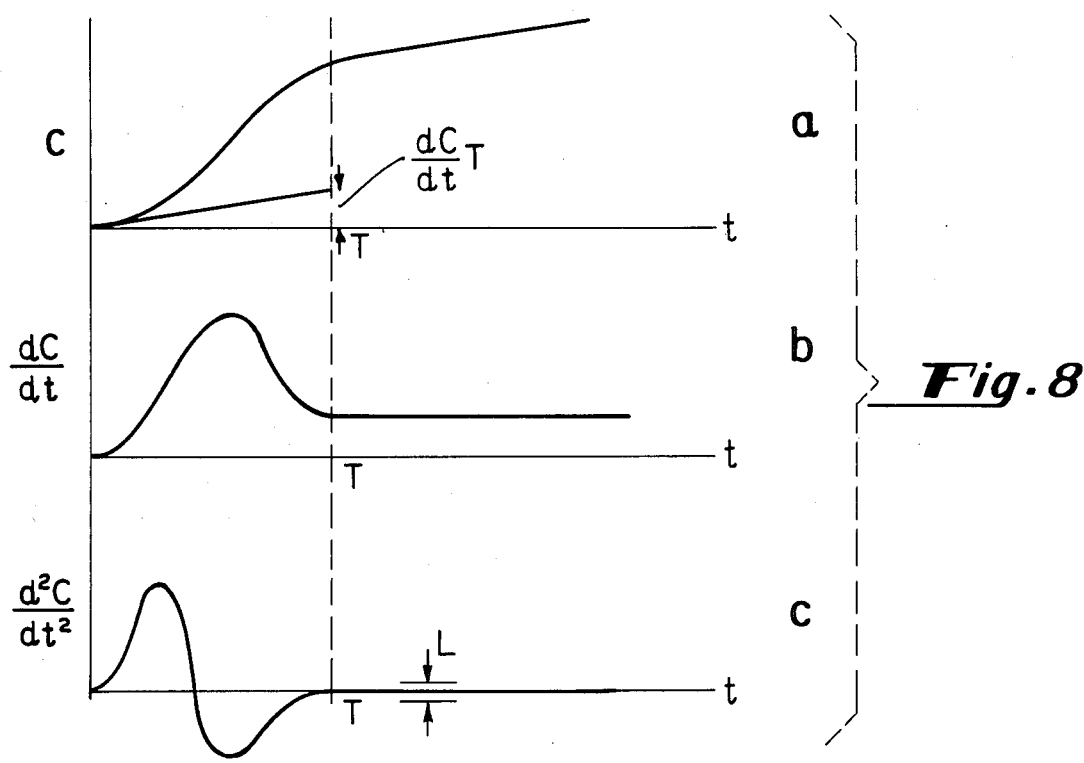

The sole difficulty with the approach just outlined is that it is not necessarily easy to determine by computer when the curve 52 has become linear. FIG. 8 shows three curves, denoted FIGS. 8a through c, which illustrate a way in which this determination can be made. FIG. 8a is a reproduction of curve 52 of FIG. 7, showing the characteristic non-linear/linear shape of the coductance versus time curve. FIG. 8b shows the time derivative of this curve, denominated dC/dt on the vertical axis, versus time. It will be observed that the first derivative essentially reaches a horizontal but non-zero value when the reaction is completed, indicated by the dashed line at time T. FIG. 8c shows the second time derivative of conductivity plotted versus time, $d^2C/dt^2$. When the value of the second derivative settles to within some small specified value L of zero, designed to account for sampling errors and the like, the conductivity curve of FIG. 8a has become linear, indicating that oxidation is complete. One can then generate a value for the correction to be applied simply by subtracting the contribution given by the instrument, (dC/dt) T, the slope of the instrument contribution curve dC/dt, times T, the time at which oxidation is determined to be complete, from the total conductivity at time T; the remainder is equal to the conductivity contribution of the carbon dioxide, which, as mentioned above, can be directly converted to a value for total organic carbon in the water sample prior to oxidation by the UV light.

Figure 9:
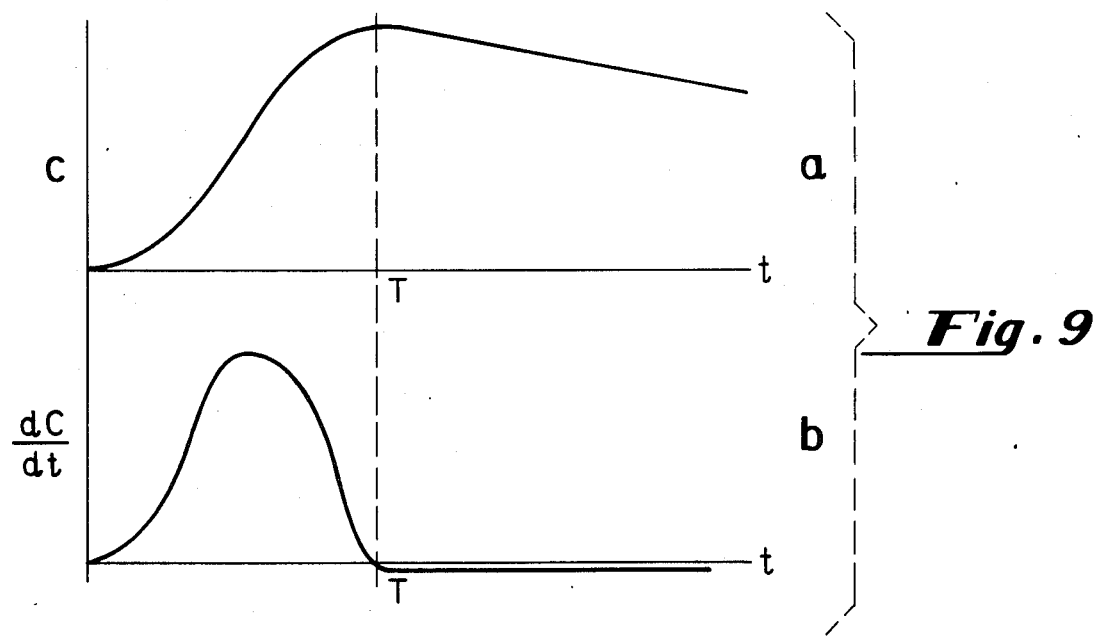

The situation just described and the curves shown in FIG. 8 occur where the contribution to the conductivity of the water of total organic carbon is relatively low compared to that caused by the instrument. In such situations, use of the second derivative approaching zero to indicate completion of oxidation approach should be used. In other cases, where the total organic carbon content is relatively high, or when the instrument is first installed, differing approaches are indicated. FIG. 9 shows such a situation, in which the conductivity of the water, shown in FIG. 9a, reaches a peak and then begins to decline. This occurs, for example, because, for example, the carbon dioxide diffuses through the water lines connected to the sample cell, reducing the conductivity of the water. It is clear, however, that once the conductivity has peaked and begun to decline, the reaction has been completed. Accordingly, the value of conductivity at this point indicates the total organic carbon content of the sample. This value can be noted readily by monitoring the time derivative of this curve, shown in FIG. 9b. When the derivative reaches zero or becomes negative, as shown, the reaction has been completed, and the conductivity at this time indicates that the amount of total organic carbon being oxidized to carbon dioxide can be generated. Here, the contribution from the electrodes is minor and can be ignored.

The applicants find that with a sample cell substantially as shown, if one simply monitors both first and second time derivatives, either the first derivative or the second derivative will approach zero, as in FIGS. 9 and 8, respectively, depending on the total organic content. The FIG. 8 curve is usually seen at TOC values less than 50 ppb, while the FIG. 9 curve becomes typical at higher TOC concentrations, the threshold being a function of actual instrument background contribution.

Those skilled in the art will recognize that there are several ways in which the first and second time derivatives as described in FIGS. 8 and 9 can be calculated and evaluated. It is envisioned that in the ultimate embodiment, dedicated analog differentiator devices could be used. Possibly these could be integrated with other circuit elements designed to indicate the total organic carbon directly. In the meantime, it will be sufficient teaching to those skilled in the art to note that a general purpose digital computer together with a conventional analog-to-digital converter device for conversion of conductivity into digital values can be used.

In a preferred embodiment which has been successfully tested, the conductivity is measured every 13 seconds, and the last 5 data points thus generated are successively curve-fit to a straight line the slope of which is monitored to determine whether the first derivative has approached the horizontal. The second derivative is generated similarly by curve-fitting five successive first derivative values to a straight line the slope of which is similarly measured. Whichever derivative first approximates zero is then used as described above in derivation of the conductivity contributed by oxidation of total organic carbon. The approach selected is thus dependent on the relative amount of total organic carbon as compared with the rate at which the instrument contributes to the conductivity of the water sample.

Figure 10:
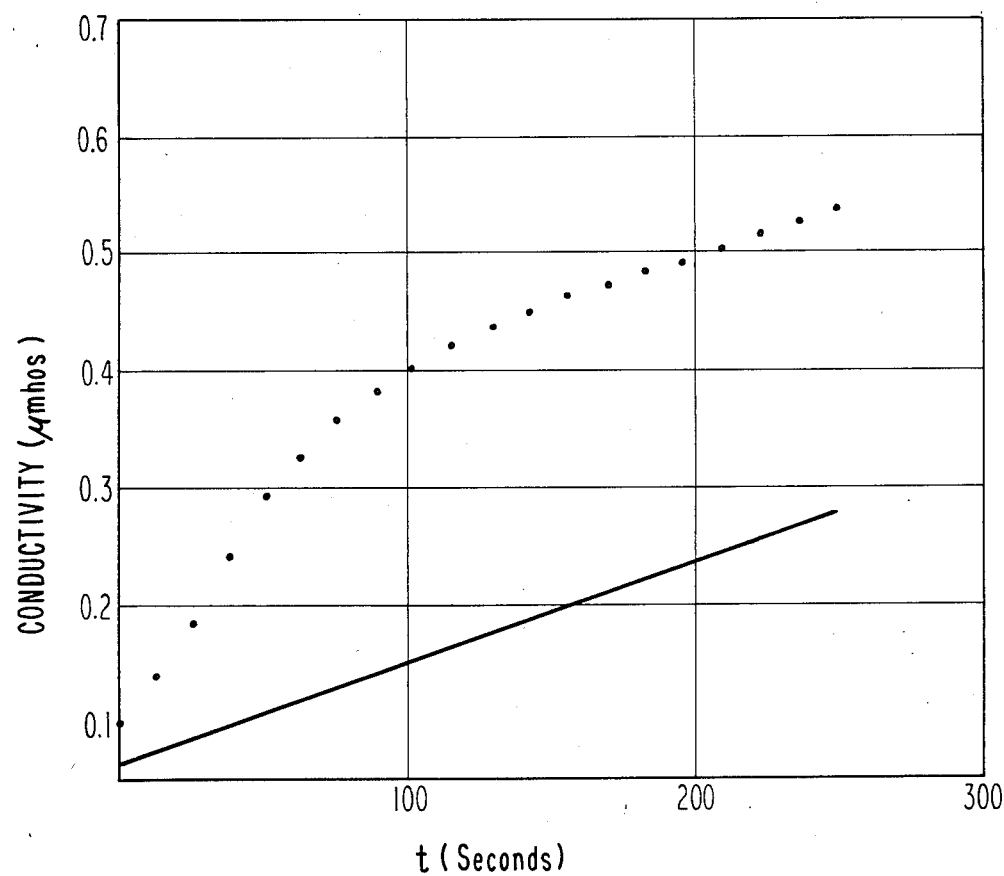
FIG. 10 shows an example of actual test data.

The following Example I is a reproduction of the output of an actual run in which the total organic content of a water sample was measured as described above. The six columns of data represent, reading left to right, sampling time, elapsed time, conductivity in micromhos, sample temperature in °C. (measured at the rear of the center electrode) and the first and second time derivatives of the conductivity measurements. The last two items mentioned do not begin until the fifth and ninth entries, due to the five-sample curve-fitting technique used, and because the first derivative is used in calculation of the second derivative. The conductivity measurements shown are graphed in the upper curve of FIG. 10. As can be observed, the curve is linear at its rightmost extremity indicating that the oxidation reaction is complete, and that further changes in conductivity are due to instrument contribution at the linear rate shown by the lower curve.

| Time (HR:MIN:SEC) | Elapsed Time (SEC) | Conductivity (MICROS) | Temp. (°C.) | DC/DT (MICROS)/SEC | D2C/DT2 (MICROS)/SEC2 |
|---|---|---|---|---|---|
| BACKGROUND MEASUREMENT | | | | | |
| 9:38:35 | 0 | .065 | 23.81 | 0 | 0 |
| LAMP ON, OXIDATION BEGINS | | | | | |
| 9:38:50 | 0 | .099 | 24.02 | 0 | 0 |
| 9:39:3 | 13 | .139 | 24.16 | 0 | 0 |

-continued

| Time (HR:MIN:SEC) | Elapsed Time (SEC) | Conductivity (MICROS) | Temp. (°C.) | DC/DT (MICROS)/SEC | D2C/DT2 (MICROS)/SEC2 |
|---|---|---|---|---|---|
| 9:39:16 | 26 | .185 | 24.32 | 0 | 0 |
| 9:39:28 | 38 | .243 | 24.49 | 0 | 0 |
| 9:39:41 | 51 | .293 | 24.67 | 3.8874803E-03 | 0 |
| 9:39:54 | 54 | .326 | 24.86 | 3.8090918E-03 | 0 |
| 9:40:6 | 76 | .357 | 25.05 | 3.3872851E-03 | 0 |
| 9:40:19 | 89 | .381 | 25.25 | 2.6544229E-03 | 0 |
| 9:40:32 | 102 | .401 | 25.42 | 2.1485315E-03 | −3.5957636E-05 |
| 9:40:45 | 115 | .42 | 25.57 | 1.8229599E-03 | −4.0926163E-05 |
| 9:40:59 | 129 | .436 | 25.73 | 1.4988779E-03 | −3.526866E-05 |
| 9:41:12 | 142 | .448 | 25.9 | 1.278984E-03 | −2.5812067E-05 |
| 9:41:25 | 155 | .462 | 26.08 | 1.1222675E-03 | −1.9353856E-05 |
| 9:41:39 | 169 | .47 | 26.21 | 9.398618E-04 | −1.6001923E-05 |
| 9:41:52 | 182 | .483 | 26.32 | 8.734737E-04 | −1.2081323E-05 |
| 9:42:6 | 196 | .491 | 26.47 | 7.912241E-04 | −9.05495E-06 |
| 9:42:19 | 209 | .502 | 26.58 | 7.4734534E-04 | −6.680404E-06 |
| 9:42:32 | 222 | .514 | 26.68 | 8.0459425E-04 | −2.872771E-06 |
| 9:42:46 | 236 | .525 | 26.83 | 7.978849E-04 | −1.039593E-06 |
| 9:42:59 | 249 | .534 | 26.96 | 8.219301E-04 | 8.10708E-07 |
| | | OXIDATION COMPLETE | | | |

Elapsed Time (Oxidation) = 4 minutes, 9 seconds
Initial Background Conductivity = .065 micromhos/cm
Final Background Conductivity = .279857 micromhos/cm
Temperature change = 3.15 degrees C.
Delta Conductivity (Instrument) = .20466059 Micromhos/cm
Delta Conductivity ($CO_2$) = .254143 micromhos/cm
TOC = 10.341327 PPB
Uncorrected TOC = 33.676432 PPB The computer output reproduced above indicates that the oxidation reaction proceeded to completion in some 4 minutes, 9 seconds, that the initial background conductivity of the water was 0.065 micromhos/cm, that it rose due to instrument contribution to a final value of 0.279 micromhos/cm and that the temperature change (used by the computer to correct the conductivity values so as to be comparable to one another) was 3.15° C. The value for L used was $10^{-6}$; after five successive values of the second derivative of the conductivity value were less than L, the change in conductivity due to the instrument was calculated to be some 0.204 micromhos/cm, and that due to oxidation of carbon was 0.254 micromhos/cm. From this last figure an initial total organic content of the water sample of some 10.3 parts per billion was calculated; if the correction for the instrument contribution had not been applied, the apparent TOC value would have been 33.6 ppb. The method of the invention of correction for this source of errors is thus clearly beneficial.

While a preferred embodiment of the invention has been snown and described, it will be appreciated that numerous other modifications and improvements thereto will be suggested to those skilled in the art. Accordingly, the invention should not be limited by the above exemplary disclosure, but only by the following claims:

We claim:

1. Apparatus for measurement of the total organic carbon content of a sample of water, comprising:
   a sample cell having a window;
   a source of ultraviolet radiaton of a frequency which causes oxidation of organic carbon compounds disposed in juxtaposition to said window, the material of said window being substantially transparent to said radiation;
   a pair of electrodes disposed in said sample cell;
   means for monitoring the conductance between said electrodes as a function of time during which a sample is exposed to ultraviolet radiation from said source;
   means for continuously calculating values for first and second time derivatives of said conductance;
   means for monitoring said values for the first and second time derivatives of the conductance; and
   means responsive to said calculated values of said second derivative for determining when said oxidation has been substantially completed.

2. The apparatus of claim 1 wherein said source of ultraviolet radiation radiates light at substantially 185.0 nanometers wavelength.

3. The apparatus of claim 1 wherein said electrodes are of generally circular shape and are concentric such that one surrounds the other and are located so as to be directly exposed to said ultraviolet radiation.

4. The apparatus of claim 1 wherein said sample cell comprises only materials which are substantially inert in the presence of water comprising organic compounds.

5. The apparatus of claim 1, wherein said means for determining when said oxidation has been substantially completed comprises means for determining when the second derivative of said conductance has substantially reached zero, and for indicating that said conductance is changing, if at all, only in a linear fashion.

6. The apparatus of claim 5 further comprising means for determining a contribution of the apparatus to the conductivity of said water sample upon determination that said second time derivative has substantially reached zero.

7. The apparatus of claim 6 further comprising means for making correction for the contribution of the instrument to the conductivity measured, comprising means for multiplying the first time derivative of the conductance at a time T when the second time derivative has reached within a predetermined range about zero by said time T and subtracting this quantity from the total conductance measured between said electrodes at time T, to provide a compensated output signal representative of conductance of the water sample due to oxidation of organic carbon compounds therein.

8. The apparatus of claim 7 further comprising means for conversion of said signal indicative of the conductance of said water sample due to oxidation of carbon compounds to a signal proportional to organic carbon content of said water prior to exposure thereof to said ultraviolet radiation.

9. A system for the measurement of total organic carbon content of a water sample containing organic matter comprising:
 a sample cell of material substantially inert to said sample of water, comprising a window;
 an ultraviolet lamp emitting radiation of frequency selected to promote oxidation of organic carbon compounds to carbon dioxide juxtaposed to said window;
 said window being of a material selected to be substantially transparent to said radiation;
 a pair of electrodes disposed in said sample cell;
 means for monitoring conductance between said electrodes as a function of time measured from the commencement of exposure of a sample of water to said ultraviolet radiation within said cell;
 means responsive to said means for monitoring for determining when the oxidation reaction has been substantially completed;
 means for separating nonlinear asymptotic variation of the conductance of said sample of water over time due to oxidation of organic carbon from substantially linear variation of said conductance over time associated with instrument contribution; and
 means responsive to said means for separating for determining the total organic carbon content of said sample of water as a function of the conductivity of said sample of water after said reaction has been completed.

10. The system of claim 9 wherein said source of ultraviolet radiation emits radiation of wavelength substantially equal to 185.0 nanometer.

11. The system of claim 9 wherein said electrodes are circular concentric electrodes mounted so that their exposed surface is flush with the surrounding surfaces of the sample cell whereby no bubbles are encouraged to collect at the junctures thereof.

12. The system of claim 11 wherein said electrodes are exposed to said ultraviolet radiation whereby fouling thereof by organic material is minimized.

13. The system of claim 9 wherein said means for determining when said reaction is completed comprises means for monitoring first and second time derivatives of said conductivity and for determinining when either derivative is substantially equal to zero, indicating that change in conductivity thereafter is linear.

14. The system of claim 13 comprising means for determining a contribution made to conductivity other than by said carbon dioxide by multiplying the first derivative of the conductivity at a time T, when the second time derivative of conductivity becomes zero, by said time T, and subtracting this quantity from the total conductivity measurement at time T, whereby the remainder is proportional to the conductivity contribution made by carbon dioxide generated by oxidation of organic material in said water sample.

15. The system of claim 14 wherein said source of ultraviolet radiation is sealed within a chamber containing no material which absorbs the ultraviolet radiation.

16. Apparatus for the real-time measurement of the total organic carbon content of a sample of water, said measurement being accurately compensated for contributions to the ionic concentration of the water sample due to sources other than said carbon, said apparatus comprising:
 a sample cell having a window therein;
 a source of radiation of a frequency which promotes oxidation of organic carbon juxtaposed to said window, said window being of material substantially transparent to such radiation;
 at least two electrodes disposed in said sample cell;
 means for generating a signal representative of the conductance of a sample of water between said electrodes;
 means for monitoring the time rate of change of said conductance signal, said means for monitoring comprising means for differentiating between a portion of the signal which is substantially linear over a given period of time and a portion which is substantially nonlinear, but which approaches an asymptotic limit during said given period of time, and means for determining when said substantially nonlinear portion of said signal approaches a stable value, indicating that the oxidation of organic carbon compounds in said sample of water due to radiation has been completed; and
 means for compensating said conductance signal value for changes in conductance of said sample of water due to factors other than variation of the ionic concentration of the sample of water caused by oxidation of said organic compounds.

17. The apparatus of claim 16 wherein said means for monitoring the time rate of change of said conductance signal comprises means for taking the first and second time derivatives of said signal and wherein said means for differentiating between the linear portion of the signal and the nonlinear portion of the signal comprises means for determining when the second derivative of said signal has reached zero.

18. The apparatus of claim 16 wherein said means for compensating comprises means for multiplying the first time derivative of the conductance signal at a time T when the second time derivative has substantially reached zero by said time T, and subtracting this quantity from the total value of said signal at said time T to provide a compensated output signal.

19. The apparatus of claim 18 further comprising means for real time temperature compensation of said conductance signal.

* * * * *